United States Patent
Lopez-Oliva Munoz

(10) Patent No.: US 8,679,119 B2
(45) Date of Patent: Mar. 25, 2014

(54) LOCKING NAIL SYSTEM FOR ARTHRODESIS RECONSTRUCTION IN CALCANEUS FRACTURES

(76) Inventor: Felipe Lopez-Oliva Munoz, Madrid (ES)

(*) Notice: Subject to any disclaimer, the term of this patent is extended or adjusted under 35 U.S.C. 154(b) by 1536 days.

(21) Appl. No.: 11/802,449

(22) Filed: May 23, 2007

(65) Prior Publication Data

US 2008/0015587 A1    Jan. 17, 2008

(30) Foreign Application Priority Data

May 24, 2006    (EP) ...................................... 06010709

(51) Int. Cl.
  *A61B 17/56*    (2006.01)
(52) U.S. Cl.
  USPC .................. 606/62; 606/64; 606/66; 606/300
(58) Field of Classification Search
  USPC ............................................ 606/62–68, 300
  See application file for complete search history.

(56) References Cited

U.S. PATENT DOCUMENTS

| | | | |
|---|---|---|---|
| 2,267,157 A * | 12/1941 | Lippincott | ...................... 606/67 |
| 4,913,137 A | 4/1990 | Azer et al. | |
| 5,179,915 A * | 1/1993 | Cohen et al. | ..................... 606/62 |
| 5,855,579 A | 1/1999 | James et al. | |
| 6,126,661 A * | 10/2000 | Faccioli et al. | .................. 606/64 |
| 6,197,029 B1 | 3/2001 | Fujimori et al. | |
| 6,579,293 B1 | 6/2003 | Chandran et al. | |
| 2006/0200141 A1* | 9/2006 | Janna et al. | ..................... 606/62 |
| 2007/0123876 A1* | 5/2007 | Czartoski et al. | ............... 606/62 |

FOREIGN PATENT DOCUMENTS

| | | |
|---|---|---|
| ES | 2164543 | 2/2002 |
| RU | 1801402 A1 | 3/1993 |
| RU | 2 157 125 C2 | 10/2000 |

OTHER PUBLICATIONS

English Language Abstract of ES 2 164 543.
English language abstract of RU 2 157 125 C2.

* cited by examiner

*Primary Examiner* — Christian Sevilla
(74) *Attorney, Agent, or Firm* — Abel Law Group, LLP

(57) ABSTRACT

Locking nail system for arthrodesis reconstruction of calcaneus fractures which includes a nail, several calcaneus-talar screws, and a guide. The system is usable for the reconstruction of severe comminuted fractures of the calcaneus in humans and fixation of this bone after reconstructing its principal form, to the talus, in order to attain arthrodesis or fusion with the latter. This Abstract is not intended to define the invention disclosed in the specification, nor intended to limit the scope of the invention in any way.

20 Claims, 4 Drawing Sheets

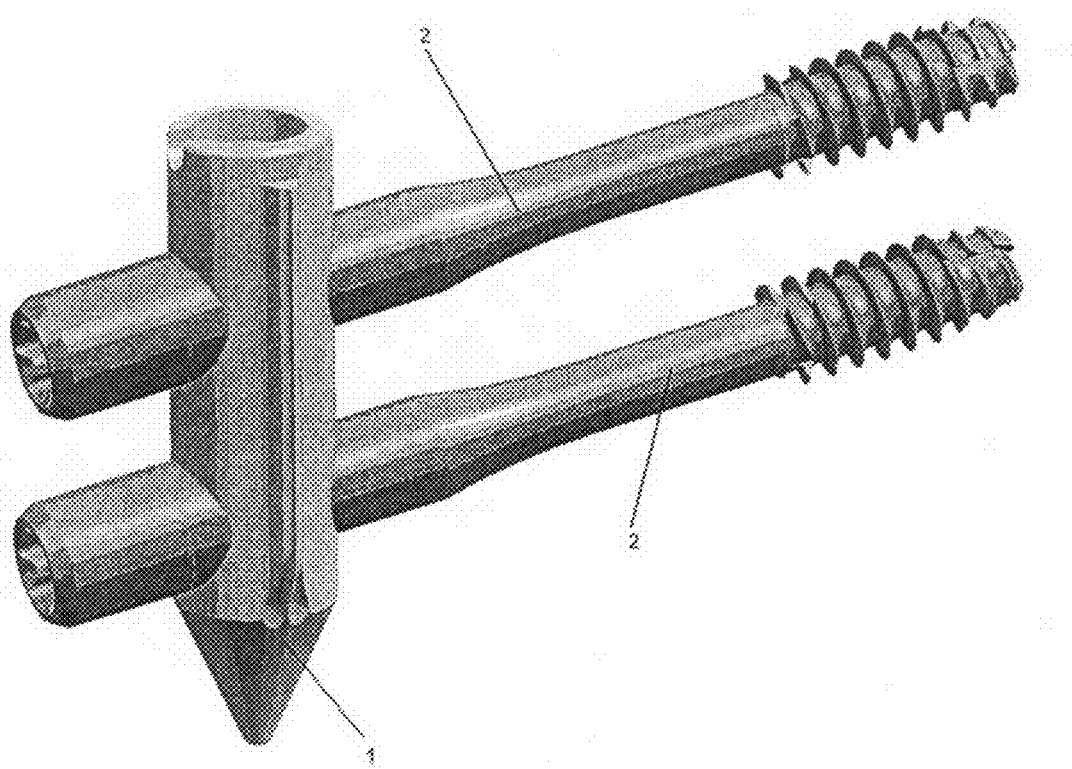

LOCKING NAIL SYSTEM FOR ARTHRODESIS RECONSTRUCTION IN CALCANEUS FRACTURES

CROSS-REFERENCE TO RELATED APPLICATIONS

The present application claims priority under 35 U.S.C.§119 of European Patent Application No. 06 010 709.1 filed May 24, 2006, the disclosure of which is hereby expressly incorporated by reference in its entirety.

BACKGROUND OF THE INVENTION

1. Field of the Invention

The invention relates to a locking nail system for arthrodesis reconstruction of calcaneus fractures. The invention can, in particular, be used in the reconstruction of severe comminuted fractures of the calcaneus in humans and fixation of this bone after reconstructing its principal form, to the talus, in order to attain arthrodesis or fusion with the latter.

2. Discussion of Background Information

Chronic residual pain is the most common sequela following comminuted talar fracture of the calcaneus. There may be multiple causes of this problem such as compartment syndrome, reflex-sympathetic dystrophy, plantar cushion syndrome, tarsal and peroneal canal syndrome, and subtalar arthritis. This latter cause has been found to be responsible for the majority of poor long-term results of current treatment of these fractures.

Talar fractures account for 8-10% of tarsal tunnel syndrome, particularly in the lateral plantar nerve branch, and for 78% of peroneal nerve entrapment (external submalleolar pain). In 70% of these severe fractures, there is chronic pain caused by the posterior subtalar joint, which normally becomes ankylosed after trauma.

Although the latest publications support the results of open reduction and internal fixation of calcaneus fractures, orthopaedic treatment still has many defenders. In other cases, the adoption of an initially conservative philosophy is chosen, treating sequelae if they appear. Like Barnard and Odegard, Applicant believes that perfect restoration of the subtalar joint is impossible.

Numerous arthrodesis techniques have been disclosed for the treatment of post-traumatic subtalar arthritis, including prosthetic replacement. In other cases, triple arthrodesis has been advocated over isolated subtalar fusion, in order to improve foot biomechanics and to prevent degeneration of adjacent joints. According to different reviews (conducted in hospitals), isolated arthrodesis of the subtalar joint does not cause degeneration of adjacent joints, even after many years of evolution.

This experience has led to the belief that the old postulations of Stulz and Noble may provide the key to a fracture that has yet to be resolved. Since the subtalar joint cannot be surgically reconstructed in the most severe fractures (and always degenerates), the solution would be to arthrodese it immediately during the acute period in order to prevent the disabling sequelaes that appear during later evolution.

However, in addition to fusing the damaged joint, an attempt should be made to reconstruct the form of the hindfoot as far as possible, in order to avoid other associated complications such as compartment syndrome, reflex-sympathetic dystrophy, plantar cushion syndrome and tarsal and peroneal canal syndromes, that would clearly benefit from fracture reduction.

Spanish publication number ES 2164543 discusses a nail that is locked by means of two screws. There are problems, however, inserting this nail into the bone because of its rectangular wedge-shaped geometry. There are also resistance problems since it has a very small section in the distal zone that also limits the securing of the lower screw.

SUMMARY OF THE INVENTION

The invention aims to alleviate the aforementioned problems by providing a new locking nail system for arthrodesis reconstruction of calcaneus fractures.

The system of the invention includes a generally cylindrical nail with two stabilising fins, a tapered point and two threaded holes. The nail is structured and arranged to be inserted into the greater tuberosity of the calcaneus. The invention also includes two cannulated screws that are screwed or threaded into the holes of the nail whereby they are inserted in the talus until they are locked in the nail. As a result, the whole system is stabilized, increasing its rigidity and resistance to loads to which it will be subjected.

The use of cannulated screws for arthrodesis of the subtalar joint is a known and implanted technique that offers amongst the best results for the treatment of this type of fracture. The locking nail system for arthrodesis reconstruction in calcaneus fractures of the present invention, however, offers a marked improvement in the technique that is habitually employed, at least because it provides for the insertion of a nail that both supports and locks the screws. This makes the system more stable and secure, and prevents failure from screw migration. As a result, the foot recovers its natural anatomy, repairing the relationship between the calcaneus and the talus, and thus recovering its biomechanical function.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 4 shows a view of the nail with two screws inserted therein according to the invention.

DETAILED DESCRIPTION OF THE INVENTION

As is apparent from FIGS. 1-5, the locking nail system for arthrodesis reconstruction in calcaneus fractures utilizes the following components: a nail 1, two screws 2, and a calcaneus-talar guide 3. The system also utilizes various devices typically used in arthrodesis reconstruction in calcaneus fractures such as guide tubes, a bit, a depth gauge, a cannulated screwdriver, a diapason impactor, a bit with limiter, and reference guide-pin.

Figures 1A, 1B, 1C:
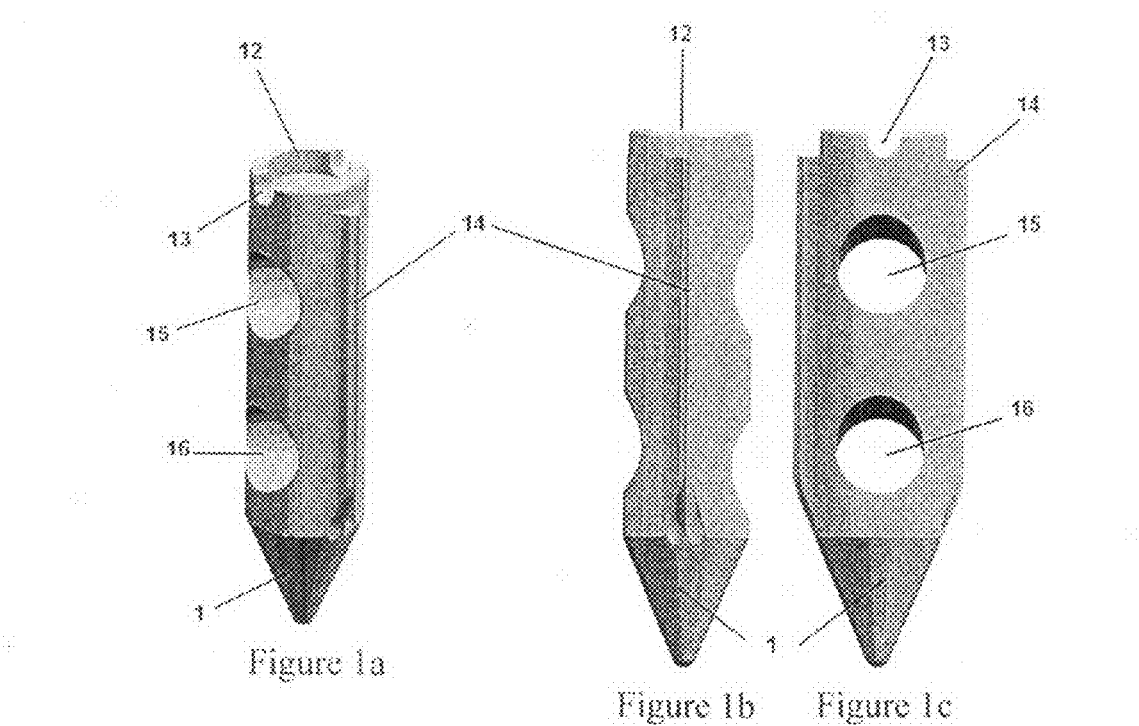
FIGS. 1a-1c shows various views of the locking nail of the invention.
Figure 2:
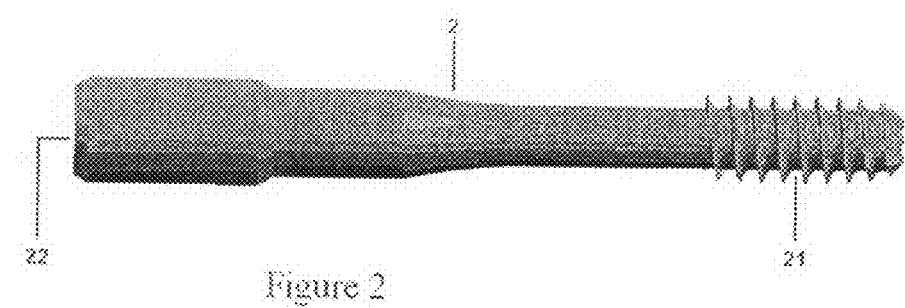
FIG. 2 shows a view of one of the cannulated screws of the invention.

As can be seen in FIGS. 1a-1c, the nail 1 is a generally cylindrical geometrical member having a tapered point end which facilitates insertion, and preferably made of metal. The other end of the nail 1 is generally blunt and includes a threaded hole 12 and a groove 13 in order to incorporate an insertion guide 33 (see FIG. 3a). The nail 1 also includes two lateral fins 14 which are generally oppositely arranged. The fins 14 function to stabilise the implant and prevent it from rotating. The nail 1 has two through holes 15 and 16 that are at least partially threaded and set at an angle of about 10° relative to a line perpendicular to a center axis of the opening 12. The openings 15 and 16 receive therein metal screws 2 (see FIG. 2) and function to arthrodese the subtalar joint using the screws 2.

The screws or calcaneus-talar screws 2 have a cannulated end 22 in order to allow for insertion with or using guide tubes. The distal end of each screw 2 has external threads 21 in order to allow the screws 2 to be fixated in the spongy bone of the talus. The tip of the distal end of each screw 2 also is preferably self-perforating and self-threading in order to facilitate insertion of the screw 2 by way of an optimum torque. The head portion of each screw 2 has an external thread (not shown) for fixing each screw 2 with respect to the nail 1 (see FIG. 4). Each screw 2 also has a hexylobe-type opening sized to receive a torque applying tool. The hexylobe-type opening guarantees a more efficient turning action. Preferably, the length of the screws 2 is not less than about 60 mm and not greater than about 90 mm.

Figure 3A:
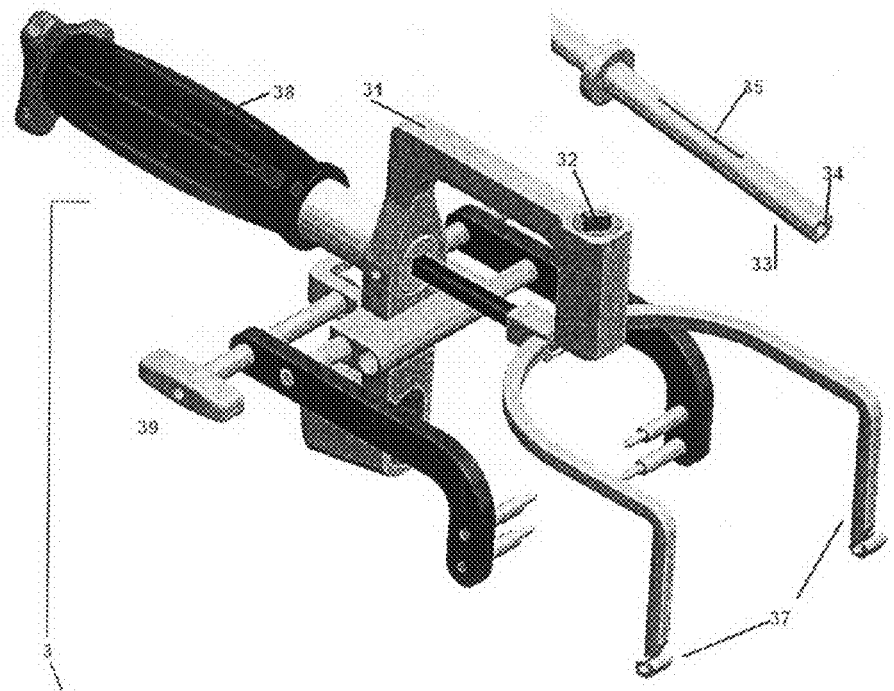
FIGS. 3a and 3b show various views of the insertion guide and a nail applicator guide which can be used to install the nail and screws according to the invention.
Figure 3B:
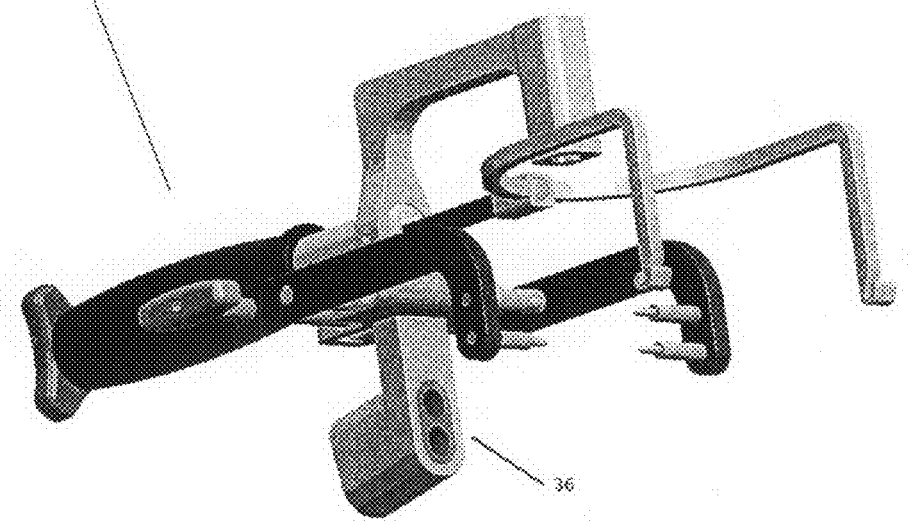
Figure 5A:
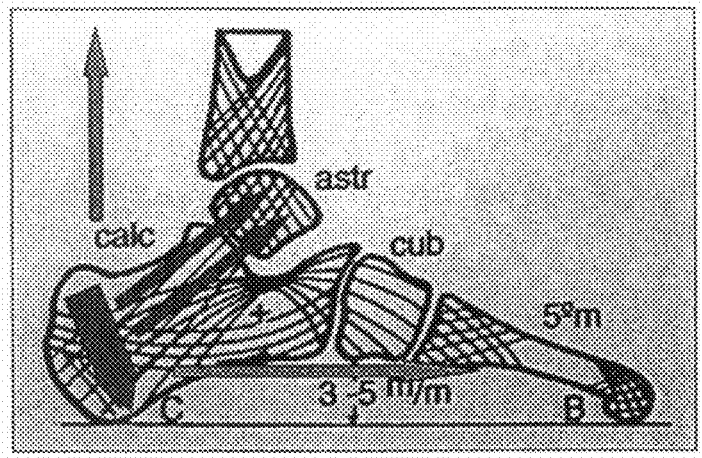
FIGS. 5a and 5b show various diagram views of the foot with the locking nail system inserted therein.
Figure 5B:
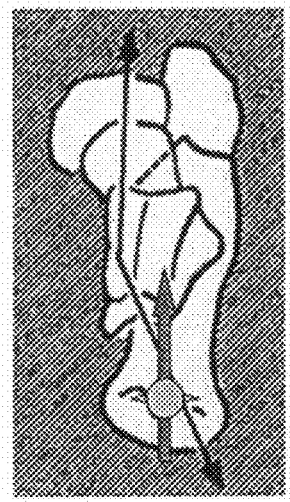

With reference to FIGS. 3a and 3b, the guide tool 3 is an instrument that is used to place the different components in the system in situ, and includes a main support 31 which has a top-side guide hole 32 whose internal geometry generally corresponds to the external geometry or configuration of the nail 1. The opening 32 is used to introduce the nail 1 using an applicator guide 33. The applicator guide 33 has an end projection 34 which fits or engages with the recess 13 of the nail 1. This ensures that its fixation is guaranteed and prevents rotation movements between the guide 33 and the nail 1. The applicator guide 33 also has a longitudinal cotter or projection 35 which functions to ensure that the nail 1 is placed at a good or proper angle in the calcaneus, through the guide hole 32.

The lower part of the guide tool 3 has a wad or guide support which includes two holes 36 that are each placed at a 10° angle with respect to a line extending perpendicular to an axis of the opening 32. The openings 36 allow portions of the whole system of cannulas and instruments to pass therethrough and permit the screws 2 to be placed in the calcaneus-talus.

The guide tool 3 also has a grip 38 that, in addition to serving as a hand grip, is connected to a jaw 37 which can be attached to a pin (not shown) that has been previously placed in the talus and which serves as a reference axis and as a support to adjust the position of the nail 1. This can occur by way of a handle that is situated at the end of the grip 38.

When using the invention, guide tubes (not shown) must be embodied in duplicate except for the trocar tip, in order to permit suitable guidance and direction of the different instruments used to prepare the bed and position the screws 2. The instruments used to prepare the bed include a guide-pin, a cannulated bit with a diameter corresponding to the nucleus of the screws 2, and the screws 2 themselves. Therefore, three guide tubes of different diameters are necessary, as well as the trocar tip. Other elements used by the system include a depth gauge to determine the length of the screws 2, a cannulated screwdriver to insert the screws 2, a diapason impactor to strike the nail 1, a bit with limiter to work the nail bed 1, and a reference pin for the guide support 3.

The implantation of the locking nail system for arthrodesis reconstruction in calcaneus fractures, according to the invention, will now be discussed in detail. First, and after opportune surgical procedures, a guide-pin is placed in the center of the talar head. The guide-pin serves as the spatial reference for the nail 1. It is placed from the internal face of the foot, locating the center of talar head using radiological means. The guide-pin should be positioned on the frontal plane parallel to the ankle joint interline, and on the axial plane, perpendicular to the foot shaft. Surgery should not be continued until it is verified that the guide-pin is in the correct position.

The guide tool 3 is initially supported by the guide-pin situated in the talar head. Then, the guide tool 3 is initially adjusted to the greater tuberosity using the handle situated at the end of the grip 38.

Radiological control is performed on the position, using guide-pins to simulate the direction of the screws 2 by inserting them in the holes 36 made for this purpose in the guide 3. The pin-guides will indicate and/or ensure the correct position of the screws 2. If they do not sit appropriately in the talar head, the guide 3 will have to be re-positioned.

At this stage, the guide 3 permits the calcaneus axis to be distracted using the handle and the grip 38, and also permits flexion-extension movements to be applied to the same, by mobilising the guide 3, using the guide-pin placed in the talar head as an axis. Then, a hole is drilled to house the nail 1 in the greater tuberosity. If the guide 3 is in the correct position, drilling of the greater tuberosity is not a problem. Drilling should continue as far as the bit limiter permits. The only precaution to take is to protect the Achiles tendon adequately.

In some cases, the severity of the comminuted fracture means that drilling will be effected on fractured bone. This situation does not pose any disadvantage for inserting the implant as the latter does not require intact bone for correct functioning. When the bit is removed, it should continue to revolve in order to extract bone dislodged during drilling. The drilling direction should not be inverted. In the majority of cases, this bone will be sufficient for the graft in the subtalar arthrodesis.

The nail 1 is held by the guide 3 and is placed in the previously marked channel. The nail 1 is inserted by hammering. The guide 3 will direct the nail 1 towards the lower zone in the greater tuberosity where it will be inserted in the plantar fascia. The nail 1 must be completely inserted up to the applicator limiter, thus attaining correct alignment of the holes of the screws 2 and the guide 3 that applies the same.

With the guide tubes in position on the guide 3, the surgeon makes a small incision reaching the bone. The guide-pin is inserted. The length of the screws 2 is measured with the depth gauge. After the guide-pin, a 4.5 mm cannulated bit is inserted. The screws 2 are then positioned. When the system is in position, the bone extracted from drilling the nail opening can be applied.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A locking nail system for arthrodesis reconstruction of calcaneus fractures comprising:
   a generally cylindrical nail comprising:
      a tapered point;
      a threaded opening;
      a groove or recess adapted to receive a portion of an applicator guide;
      two lateral fins; and
      two through openings that are at least partially threaded and oriented at an angle of about 10° relative to a line perpendicular to an axis of the threaded opening;
   plural calcaneus-talar screws each comprising:
      a cannulated end adapted to be guided by a guide tube;
      a threaded distal end adapted to be fixated in spongy bone of a talus;
      a self-perforating and self-threading tip;
      a head for fixing the screw in the nail; and
      a hexylobe-type opening;
   a guide comprising:
      a main support utilizing a guide hole having a geometry which generally corresponds to an external geometry of the nail, the guide hole allowing for introduction of the nail using the applicator guide;
      a lower support having two openings;
      a grip connected to a jaw attachable to a pin that has been previously placed in the talus and that serves as a reference axis and as a support to adjust a position of the nail by way of a handle that is situated at an end of the grip; and
   at least one of the following:
      guide tubes;
      a bit;
      a depth gauge;
      a cannulated screwdriver;
      a diapason impactor;
      a bit with limiter; and
      a reference guide-pin.

2. The system of claim 1, wherein the guide tubes comprise duplicate guide tubes except for the trocar tip, whereby the system permits suitable guidance and direction of different instruments used to prepare a bed and position the screws.

3. The system of claim 1, wherein the depth gauge is adapted to determine a length of the screws, the cannulated screwdriver is adapted to insert the screws, the diapason impactor is adapted to strike the nail, the bit with limiter is adapted to work the nail, and the reference guide-pin is adapted for use with the guide.

4. The system of claim 1, wherein the system is structured and arranged to implant an implant in a user's foot comprising the nail and the screws, and wherein two fins stabilise the implant and prevent it from rotating.

5. The system of claim 1, wherein the through openings are structured and arranged to permit the subtalar joint to be arthrodesed using the screws.

6. The system of claim 1, wherein at least one of the screws comprises a length that is between about 60 mm and about 90 mm.

7. The system of claim 1, wherein the applicator guide comprises an end projection configured to engage with the recess of the nail and a longitudinal projection adapted to ensure placement of the nail at a desired angle in the calcaneus and insertion through the guide hole.

8. A locking nail system for arthrodesis reconstruction of calcaneus fractures comprising:
   a generally cylindrical metal nail comprising:
      a blind opening;
      a groove or recess adapted to receive a portion of an applicator guide;
      lateral fins; and
      two through openings that are at least partially threaded;
   plural screws each comprising:
      a cannulated end adapted to be guided by a guide tube;
      a threaded distal end adapted to be fixated in spongy bone of a talus;
      a self-perforating and self-threading tip; and
      a head for fixing the screw in one of the two through openings of the nail;
   a guide comprising:
      a main support utilizing a guide hole having a geometry which generally corresponds to an external geometry of the nail, the guide hole allowing for introduction of the nail using the applicator guide;
      another support having two openings; and
      a grip connected to a jaw attachable to a pin that has been previously placed in the talus and that serves as a reference axis and as a support to adjust a position of the nail by way of a handle that is situated at an end of the grip.

9. The system of claim 8, further comprising:
   a depth gauge adapted to determine a length of the screws;
   a cannulated screwdriver adapted to insert the screws;
   a diapason impactor adapted to strike the nail;
   a bit with limiter adapted to work the nail; and
   a reference guide-pin adapted for use with the guide.

10. The system of claim 8, wherein the system is structured and arranged to implant an implant in a user's foot comprising the nail and the screws, and wherein two fins stabilise the implant and prevent it from rotating.

11. The system of claim 8, wherein the through openings are structured and arranged to permit the subtalar joint to be arthrodesed using the screws.

12. The system of claim 8, wherein at least one of the screws comprises a length that is between about 60 mm and about 90 mm.

13. The system of claim 8, wherein the applicator guide comprises an end projection configured to engage with the recess of the nail and a longitudinal projection adapted to ensure placement of the nail at a desired angle in the calcaneus and insertion through the guide hole.

14. A locking nail system for arthrodesis reconstruction of calcaneus fractures comprising:
   a metal nail comprising:
      a proximal end having an opening and a recess adapted to receive a portion of an applicator guide;
      oppositely arranged projections; and
      two through openings;
   plural screws each comprising:
      a cannulated end adapted to be guided by a guide tube;
      a threaded distal end adapted to be fixated in spongy bone of a talus;
      a self-perforating and self-threading tip; and
      a head for fixing the screw in one of the two through openings of the nail;
   a guide comprising:
      a main support utilizing a guide hole allowing for introduction of the nail using the applicator guide;
      another support having two openings;
      a grip; and
      an adjustably movable jaw;
   and further comprising:
      a depth gauge adapted to determine a length of the screws;

a cannulated screwdriver adapted to insert the screws;
a diapason impactor adapted to strike the nail;
a bit with limiter adapted to work the nail; and
a reference guide-pin adapted for use with the guide.

15. The system of claim 14, wherein the system is structured and arranged to implant an implant in a user's foot comprising the nail and the screws, and wherein two fins stabilise the implant and prevent it from rotating.

16. The system of claim 14, wherein the through openings are structured and arranged to permit the subtalar joint to be arthrodesed using the screws.

17. The system of claim 14, wherein at least one of the screws comprises a length that is between about 60 mm and about 90 mm.

18. The system of claim 14, wherein the applicator guide comprises an end projection configured to engage with the recess of the nail and a longitudinal projection adapted to ensure placement of the nail at a desired angle in the calcaneus and insertion through the guide hole.

19. A method of using the system of claim 14 for arthrodesis reconstruction of calcaneus fractures, the method comprising:
   implanting with the guide an implant in a user's foot comprising the nail and the screws.

20. A method of using the system of claim 1 for arthrodesis reconstruction of calcaneus fractures, the method comprising:
   implanting with the guide an implant in a user's foot comprising the nail and the screws.

* * * * *